United States Patent [19]

Matolcsy et al.

[11] Patent Number: 4,672,112

[45] Date of Patent: Jun. 9, 1987

[54] β-CYCLODEXTRINE COMPLEX OF BENZENE SULPHONYL UREA DERIVATIVES

[75] Inventors: György Matolcsy; Antal Gimesi; Krisztina Pelejtei née Bauer; Janisz Sztatisz; Ágota Tombor née Szotyori; Tibor Cserháti; Anikó Gerlei née Komáromy; Mariann Kardos née Nikoletti, all of Budapest; József Dukai, Veszprém; Dezso Sebok, Veszprém; Csaba Söptei, Veszprém; Lajos Nagy, Fuzfögyártelep; Iván Bélai, Budapest, all of Hungary

[73] Assignees: Magyar Tudomenyos Akademia Novenyvedelmi Kutato Intezete; Nitrokemia Ipartelepek, both of Budapest, Hungary

[21] Appl. No.: 742,218

[22] Filed: Jun. 6, 1985

[30] Foreign Application Priority Data

Jun. 8, 1984 [HU] Hungary .................. 2216/84

[51] Int. Cl.⁴ .................. C08B 37/16; A61K 31/73
[52] U.S. Cl. .................. 536/46; 71/66; 71/90; 71/92; 514/58
[58] Field of Search .................. 514/58; 536/46; 71/66, 71/90, 92

[56] References Cited

U.S. PATENT DOCUMENTS

| 4,127,405 | 11/1978 | Levitt | 71/93 |
| 4,169,719 | 10/1979 | Levitt | 71/92 |
| 4,482,709 | 11/1984 | Iwao et al. | 536/46 |
| 4,518,588 | 5/1985 | Szejtli et al. | 536/46 |
| 4,524,068 | 6/1985 | Szejtli et al. | 514/58 |

*Primary Examiner*—Ronald W. Griffin
*Attorney, Agent, or Firm*—Mandeville and Schweitzer

[57] ABSTRACT

A new and improved herbicidal and plant growth regulating composition, and the method of manufacturing that composition. The new complex composition of the invention is an inclusion complex of one more benzene sulphonyl urea derivative of the general formula (II)

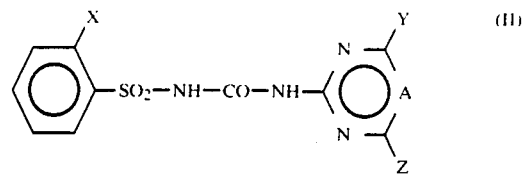

and two or more moles of beta cyclodextrine of the formula (I).

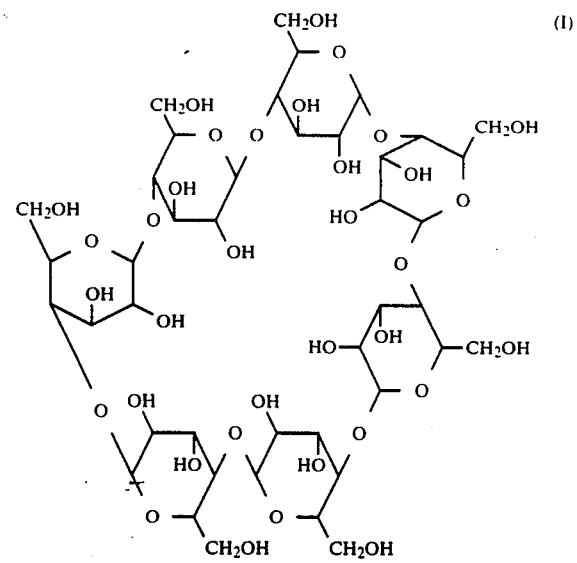

10 Claims, 1 Drawing Figure

β-CYCLODEXTRINE COMPLEX OF BENZENE SULPHONYL UREA DERIVATIVES

BACKGROUND OF THE INVENTION

The present invention is related to herbicidal agents and to plant growth regulators containing as active ingredient the complex of a benzene sulphonyl urea derivative of the general formula (II)

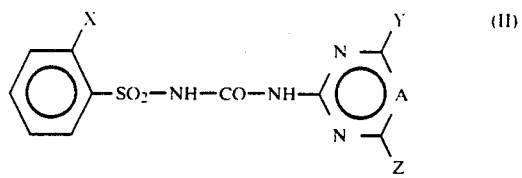

and of β-cyclodextrin of the formula (I)

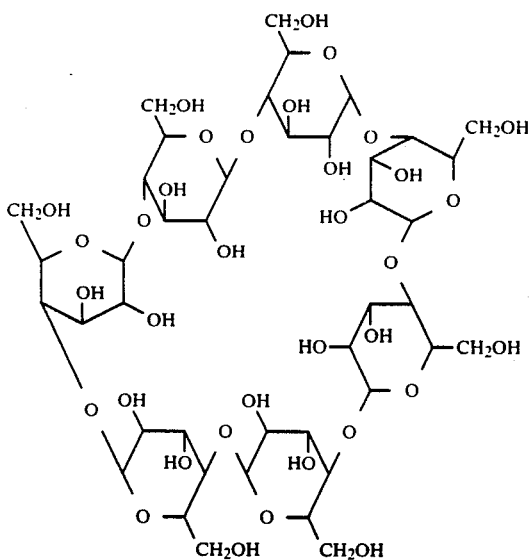

as well as the use of these compositions in plant protection and a process for the preparation of the active ingredient complexes.

Related to 1 mole of the benzene sulphonyl urea derivative of the general formula (II) at least 2 moles of cyclodextrine are needed in order that the whole amount of the sulphonyl urea forms a cyclodextrine inclusion complex. Accordingly the new complex of the invention is an inclusion complex of 1 mole sulphonyl urea derivative of the general formula (II) with 2 or more cyclodextrine molecules.

In the general formula (II)

X stands for halogen or —COOR— wherein R stands for an aliphatic group;

Y and Z independently of each other stand for hydrogen, $C_{1-4}$ alkyl or $C_{1-4}$ alkoxy and A represents a —$CH_2$— group or nitrogen atom.

R preferably stands for alkyl, alkenyl or alkinyl having up to 4 carbon atoms particularly methyl, ethyl or propyl. As halogen chlorine is preferred. Y and Z preferably stand for methyl or methoxy.

In U.S. Pat. Nos. 4,169,719 and 4,127,405 benzene sulphonyl urea derivatives of the general formula (II) were described as active ingredients of selective herbicidal agents—wherein X, Y, Z and A are as given above—. Due to the high efficiency they are suitable for application in small amounts related to 1 ha and their use is also favourable from the point of view of toxicity. Both their acute and chronic toxical dosage are extremely high [J. Agric. Food Chem. 29, 416 (1981)]. In certain cases when using higher dosages it was observed that the decomposition of the active ingredients is very slow and so in case of sensitive plant cultures the persistance of the active ingredients should be taken into account [Byeung Hoa Kang: Verhalten and Verbleib Sowie Ursachen für die selektive Wirkung von Chlorsulfuron in Kulturpflanzen and Unkräutern, Inst. für Phytomedizin der Univ. Hohenheim DBR, September 1983].

SUMMARY OF THE INVENTION

We have now found that the benzene sulphonyl urea derivatives of the general formula (II) can be complexed with β-cyclodextrine and the compositions containing these complexes show a better activity than compositions containing only benzene sulphonyl urea derivatives of the general formula (II) and in a small dose they are suitable for plant growth regulation and further their persistence is reduced. The plant growth regulating activity of the compositions containing compounds of the general formula (II) has not been known.

β-Cyclodextrine of the formula (I) is a compound forming a great ring molecule consisting of seven glucose rings [Cramer-Hettler: Naturwise. 54, 625-632 (1967)].

The complexes according to the invention as active ingredients of plant protecting agents are due to the hydroxyl groups of the molecule more hydrophylic than bezene sulphonyl urea of the general formula (II) thus their solubility in water is better, they can be handled and processed to plant protecting agents by a simpler way. The water solubility of benzene sulphonyl urea derivatives of the general formula (II) is rather poor which makes their processing into plant protecting agents more complicated.

As a consequence of the good stability of the complexes they can be stored without decomposition for a long time. Under green-house conditions the herbicidal activity of the complexes is at least the same as the activity of benzene sulphonyl urea derivatives of the general formula (II) but generally the activity of the new complexes surpasses this activity. According to the free land test results the complex of the invention when applied at the same dose is as efficient or more efficient than the most efficient representative of the known herbicides of the type sulphonyl urea in spite of the fact that the sulphonyl urea part represents only a part i.e. 1/6 of its molecule. This means an economical advantage as the amount of the expensive sulphonyl urea which can be prepared only by a technology consisting of several steps, can be considerably reduced. The use of the complex according to the invention further decreases the contamination of the soil with chemicals as a greater portion of the complex is formed by an oligosacharide which is closely related to the natural sugars and thus cannot be considered as being a chemical soil contaminating agent.

When using the complex in a small dose, preferably post-emergence, the complex stimulates the growth of plants.

The complex can be prepared by reacting at least 2 moles β-cyclodextrine with 1 mole benzene sulphonyl urea derivatives of the general formula (II). One may preferably proceed by adding to an aqueous alcoholic solution of β-cyclodextrine a suspension of benzene sulphonyl urea derivative in a water miscible solvent at a temperature ranging between room temperature and 50° C. The reaction is somewhat exotherm. The reaction mixture is stirred for 2 to 6 hours whereafter the reaciton mixture is preferably evaporated at room temperature. A preferred molar ratio of the benzene sulphonyl urea derivative and β-cyclodextrine is 1 to 2.

The formation of the complex which is a new compound was proved by thermoanalysis and it was identified. The thermoanalytical method (TEA=Thermal Evolution Analyzer) is suitable for showing the formation of the complex, if the free benzene sulphonyl urea used for the complex formation evaporates or decomposes at a lower temperature than the decomposition temperature of β-cyclodextrine which is 300° C. The formation of the complex is proved if its decomposition occurs at a higher temperature than the decomposition point of the molecule forming a complex with β-cyclodextrine.

DESCRIPTION OF PREFERRED EMBODIMENTS

Figure 1:
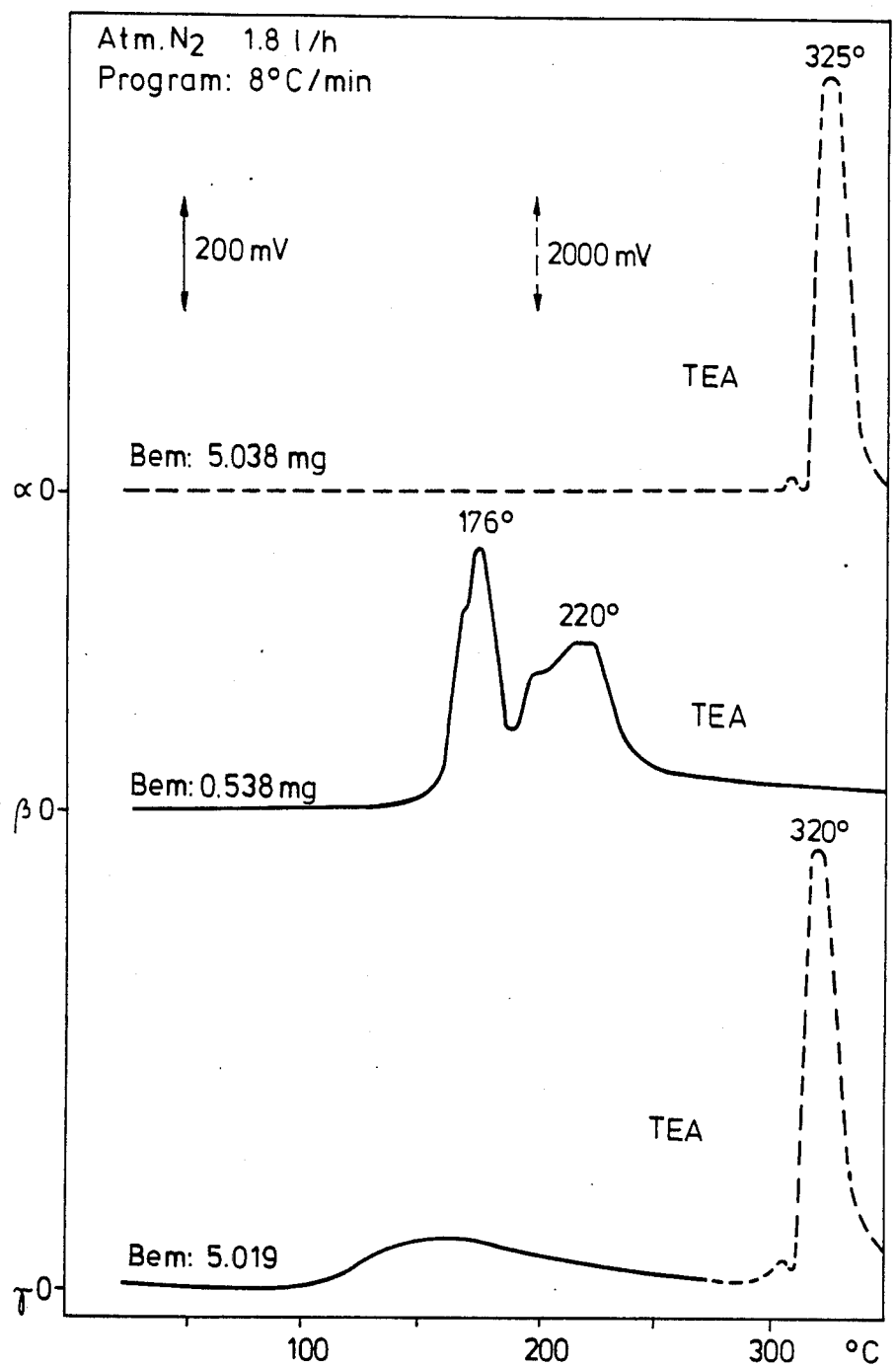
FIG. 1 is a graph showing α the thermoanalytical curve of the β-cyclodextrine and β of the sulphonamide derivative and γ of the complex.

The test sample was placed into an oven and the oven was heated at a linear rate of 8° C./minute. In a given temperature range the decomposition product leaving the sample was led to a flame ionization detector by means of inert gas (1.8 l./minute nitrogen). The detector gives a signal which is proportionate to the organic substance content leaving the sample. The temperature range refers to the quality of the left material and the surface below the curve shows its amount. *Sztatisz, J. Gal, S. Komives J. Stadler-Szoke A.—Szeijtli J.: Thermoanalytical Investigation on Cyclodextrine Inclusion Compounds. Thermal Analysis Proc. 6th Bayreuth HGW Jedemann Birkhaeusen Verlag, Basel, 1980. p. 487-493.*].

In the following Examples showing the process of the invention the temperature range of the decomposition of the complex and the benzene sulphonyl urea derivative as well as the thermoanalytical curve are given.

EXAMPLE 1

N-[(4-Methoxy-6-methyl-1,3,5-triazin-2-yl)aminocarbonyl]-2-chlorobenzene-sulphonamide β-cyclodextrine complex To an aqueous solution of 2 mole β-cyclodextrin containing 30% ethanol at 37° C. a 37° C. warm suspension of 1 mole 4-[(4-methoxy-6-methyl-1,3,5-triazin-2-yl)-aminocarbonyl]-2-chlorobenzene-sulphonamide in a water miscible solvent is added dropwise. The reaction mixture is vigorously stirred for 4 hours at 37° C. and evaporated to dryness at room temperature and the title complex is obtained. Molecular weight: 2627.5 According to TEA method the complex decomposes above 280° C. and the decomposition range of the benzene sulphonyl urea derivatives is between 160° to 240° C. Referring to FIG. 1, the decomposition of α (upper curve) is started only above 300° C., the TEA peak occurring at 300°-350° C. is characteristic for the decomposition. Up to 300° C. no organic substance releases from cyclodextrin.

As shown by curve β the benzene decomposition is started at 130° C. and under the circumstances of the test the decomposition still continues at 350° C. A double peak occurring at 150°-250° C. is characteristics for the decomposition.

On curve γ at 100°-250° C. organic substance is released from the complex sample which is characteristic for the release of the uncomplexed "free" active ingredient. It can be observed that the uncomplexed active ingredient is released at somewhat lower temperature than the pure active ingredient (middle curve), and this can be explained as follows: the uncomplexed active ingredient is placed on the surface of BCD as a carrier and thus is decomposed at a greater surface.

The active ingredient bound in complex form decomposes—releases—only above 300° C., simultaneously with the decomposition of cyclodextrin as it is shown by the peak occurring at 300°-350° C.

Preparation of the starting materials:

(A) 2-Chlorobenzene-sulphonyl-chloride is prepared according to DE PS No. 23 08 262, (B) 6-methyl-4-methoxy-2-amino-triazine is prepared according to JP PS Nos. 66-92 and 66-1115, (C) intermediate products according to (A) and (B) are reacted according to the method disclosed in European PS No. 34 431.

EXAMPLE 2

N-[(4,6-Dimethyl-pyrimidin-2-yl)-aminocarbonyl]-2-(methoxycarbonyl)-benzene-sulphonamide-β-cyclodextrin complex One may proceed as disclosed in Example 1 by reacting the corresponding benzene sulphonyl urea with β-cyclodextrin at a molar ratio of 1:2. Molar weight of the complex: 2634.

According to determination by TEA method the complex is decomposed at above 230° C. and the decomposition temperature range of the benzene-sulphonyl urea derivative is 170°-230° C.

The preparation of the starting materials:

(A) 2-methoxycarbonyl)-benzene-sulphonamide is prepared according to J. Org. Chem. 27, 1703-1709 (1962) and according to European PS No. 46 626, (B) 2-amino-4,6-dimethyl-pyrimidine can be prepared according to U.S. Pat. No. 2,660,579, (C) compounds according to (A) and (B) can be reacted according to Example 1 (C).

EXAMPLE 3

N-[(4-Methoxy-6-methyl-1,3,5-triazin-2-yl)amino-carbonyl]-2-(methoxycarbonyl)-benzene-sulphonamide-β-cyclodextrin complex The compound is prepared as disclosed in Example 1 by reacting the corresponding benzenesulphonyl-urea with β-cyclodextrin at a molar ratio 1:2. Molecular weight of the copmlex: 2651.

According to TEA method the complex is decomposed at above 230° C. and the decomposition temperature range of the benzene-sulphonyl-urea derivative is 150°-230° C.

Preparation of the starting compounds:

(A) 2-(methoxycarbonyl)-benzene-sulphonamide can be prepared according to Example 2 (A).

(B) 6-methyl-4-methoxy-2-amino-triazine is prepared according to Example 1 (B).

(C) compounds according to (A) and (B) can be reacted by a method of Example 1(C).

EXAMPLE 4

N-[(4,6-Dimethyl-pyrimidin-2-yl)-aminocarbonyl]-2-chlorobenzene-sulphonamide-$\beta$-cyclodextrin complex The compound is prepared as disclosed in Example 1 by reacting the corresponding benzenesulphonyl urea with $\beta$-cyclodextrin at a molar ratio of 1:2. Molecular weight: 2610.5.

According to the determination by TEA method the complex is decomposed at a temperature above 280° C. and the decomposition temperature range of the benzenesulphonyl-urea derivatives is 150°–240° C.

The preparation of the starting materials:
(A) 2-chloro-benzene-sulphonylchloride is prepared according to Example 1(A),
(B) 2-amino-4,6-dimethyl-pyrimidine is prepared according to Example 2(B),
(C) compounds according to (A) and (B) can be reacted by a method according to Example 1(C).

The new agents containing the complexes can be used in the form usually accepted in agriculture such as solutions, emulsions, concentrates, suspensions, dispersions, dusts, granulates, etc. which are suitable for the treatment of the plants pre- or postemergence. Due to the good water solubility of the complexes agents are preferred which are prepared with water or can be diluted with water prior to use. The compounds prepared with water can preferably contain surfactants which promote the adhesion of the agents to the plants and their penetration to the plant tissue.

The new plant protecting agents according to the invention contain the complexes in an amount of 0.1–95 percent by weight together with the usual carriers, such as solid or liquid carriers or diluting agents and optionally surfactants. The herbicides or plant growth regulators according to the invention can be in the concentrated form or can be diluted inform suitable for direct use.

In order to prepare the new compositions liquid carriers of diluting agents can be used, such as aliphatic, aromatic and cyclic hydrocarbons or derivatives thereof, mineral oil fractions or highly polar solvents. As an example methanol, propanol, cyclohexane, cyclohexanol, dimethylformamide, dimethylsulphoxide, chlorinated hydrocarbons, water can be mentioned. The solid carriers or diluting agents can be natural or artificial and can be used in powdered or granulated form. As a solid carrier kaolin, silicate, talc, dolomite, siliceous earth, wood-filings or sawdust may be used.

As surfactants ionogen or non-ionogen dispersing, emulsifying agents or wetting agents can be mentioned, such as alkylbenzene or alkyl-naphthaline sulphonate, sulphated fatty alcohol, esters of sodium sulphosuccinate, sulphonated or sulphated fatty acid ester, poly(oxyethylene)-glycol-ester, alkyl-aryl-polyethoxy-alcohol, condensate of castor oil and ethyleneoxide, sorbitan fatty acid ester, calcium and amine salts of fatty alcohol sulphate, etc.

As suitable surfactants we refer to the manual Surfactant Science Series (Marcel Dekker, Inc. New York). Some typical compositions according to the invention are shown in the following Examples.

FORMULATION EXAMPLES

EXAMPLE I

Wettable powder 40 parts by weight of active ingredient according to Example 1, 55 parts by weight of kaolin, 2.5 parts by weight of fatty alcohol sulphonate and 2.5 parts by weight of sulfite. Waste liquor are admixed and ground in a vibration mill. The obtained wettable powder contains 40% by weight of active ingredient can be suspended in water and sprayed.

EXAPMLE II

Wettable powder 10 parts by weight of active ingredient according to Example 2, 5 parts by weight of oxyethylated anhydrosorbit-monostearate (Tween 60), 85 parts by weight of kaolin are ground together and a wettable powder is obtained which contains 10% by weight of active ingredient, which can be diluted with water and sprayed.

EXAMPLE III

Emulsifyable concentrate 95 parts by weight of active ingredient according to Example 3 and 5 parts by weight of Tween 60 are admixed and a 95% by weight concentrate is obtained which can be diluted with water.

EXAMPLE IV

Aqueous spray liquid 7 parts by weight of active ingredient according to Example 4 are dissolved in 93 parts by weight of water. The solution is suitable for direct use by spraying.

EXAMPLE V

Aqueous suspension 45 parts by weight of active ingredient according to Example 1, 0.5 parts by weight of sulfite waste liquor, 0.5 parts by weight of fatty alcohol sulphonate and 54 parts by weight of water are admixed and the suspension is obtained which can be diluted with water prior to use.

BIOLOGICAL EXAMPLES

EXAMPLE VI

The new herbicidal and plant growth regulating agents containing the complexes according to the invention were tested in green house and as well on free land by using cultivated plants and weeds. The treatment was carried out pre- and postemergence by using the aqueous solution of the active ingredients of Examples 1–4. As a comparative agent N-[(4-methoxy-6-methyl-1,3,5-triazin-2-yl)-amino-carbonyl]-2-chloro-benzene-sulphonamide was used (Chlorsulfuron).

For the green house test the active ingredients were used dispersed in 1000 l. of water pro ha. at an amount of 300 g./ha. This amount corresponds to 50 g./ha. of benzene sulphonyl urea derivative. The known benzene sulphonyl urea was used at a rate of 50 g./ha. The evaluation was carried 8–16 days after the treatment. The results of the green house tests are summarized in Table I.

Under free land conditions the herbicidal effect of an agent containing N-[(4-methoxy-6-methyl-1,3,5-triazin-2-yl)-amino-carbonyl]-2-(methoxycarbonyl)benzene-sulphonamide β-cyclodextrin complex was tested pre- and postemergence in different concentrations comparing its activity with the activity of the composition containing only N-[(4-methoxy-6-methyl-1,3,5-triazin-2-yl)-aminocarbonyl]-2-chlorobenzene sulphonamide. (Chlorsulfuron). The active ingredient was dispsersed per ha. in 1000 l. water and an amount of 30, 60 and 120 g./ha. was applied (related to the benzenesulphonyl urea derivative it corresponds to 5, 10 and 20 g./ha.). The known active ingredient was used at a rate of 20 g./ha.

The evaluation was carried out 10 days after the treatment and the results are summarized in Table II.

The plant growth regulating activity of N-[(4-methoxy-6-methyl-1,3,5-triazin-2-yl)-aminocarbonyl]-2-(methoxycarbonyl)-benzene-sulphonamide β-cyclodextrin complex was tested and as a comparative agent a known plant growth regulator called Wuxal was used containing sodium, phosphorus, potassium, magnesium as well as trace elements such as iron, zinc, manganese, boron, copper, molybdene and cobalt as well as chelate forming hormones. The treatment was performed by spraying 10–20 cm. Zea mays and the composition was used dispersed in 1000 l. water at a rate of 5000, 1000 and 100 g./ha. The amount of Wuxal amounted to 5000 g./ha.

The evaluation was carried out 17 days after the treatment and the green weight of the plants was compared with the untreated control. The results are summarized in Table III.

The following plants and weeds were used for the biological tests:

Plants

Zea mays (mayz)
Triticum vulgare (winter wheat)
Hordeum distichon (summer wheat)
Beta vulgaris (sugar beet)
Trifolium pratense (red clover)

Weeds

Sinapis alba (white mustard)
Panicum capillare (sorghum)
Setaria viridis (green bristle grass)
Echinochloa crus-galli (barnyard grass)

TABLE I

| Testplant | 1 pre | 1 post | 2 pre | 2 post | 3 pre | 3 post | 4 pre | 4 post | known pre | known post |
|---|---|---|---|---|---|---|---|---|---|---|
| Plants: | | | | | | | | | | |
| Zea mays | 30 | 50 | 80 | 100 | 0 | 0 | 90 | 0 | 25 | 40 |
| Triticum vulgare | 0 | 0 | 0 | 0 | 0 | 0 | 0 | ·0 | 0 | 0 |
| Hordeum distichon | 0 | 0 | 0 | 0 | 0 | 0 | 0 | 0 | 0 | 0 |
| Trifolium pratense | 5 | 100 | 0 | 100 | 0 | 100 | 5 | 100 | 45 | 100 |
| Weeds: | | | | | | | | | | |
| Sinapis alba | 100 | 100 | 100 | 100 | 100 | 100 | 100 | 100 | 80 | 100 |
| Panicum capillare | 20 | 10 | 30 | 100 | 0 | 0 | 30 | 0 | 5 | 0 |
| Setaria viridis | 0 | 80 | 20 | 100 | 0 | 25 | 0 | 100 | 0 | 85 |
| Echinochloa crus-galli | 0 | 45 | 0 | 100 | 0 | 0 | 20 | 0 | 0 | 70 |

0 = no injury
100 = entire killing
pre = pre-emergence
post = post-emergence

TABLE II

| test plant | Active ingredient according to Example 1 | | | | | | Known | |
|---|---|---|---|---|---|---|---|---|
| | pre 30 g./ha. | post 30 g./ha. | pre 60 g./ha. | post 60 g./ha. | pre 120 g./ha. | post 120 g./ha. | pre 30 g./ha. | post 30 g./ha. |
| Plants: | | | | | | | | |
| Zea mays | 0 | 0 | 10 | 30 | 30 | 50 | 0 | 40 |
| Triticum vulgare | 0 | 0 | 0 | 0 | 0 | 0 | 0 | 0 |
| Hordeum distichon | 0 | 0 | 0 | 0 | 0 | 0 | 0 | 0 |
| Trifolium pratense | 0 | 30 | 50 | 100 | 100 | 100 | 45 | 100 |
| Weeds: | | | | | | | | |
| Sinapis alba | 100 | 100 | 100 | 100 | 100 | 100 | 100 | 100 |
| Panicum capillare | 0 | 0 | 30 | 100 | 50 | 100 | 0 | 0 |
| Setaria viridis | 20 | 25 | 20 | 100 | 100 | 100 | 0 | 15 |
| Echinochloa crus-galli | 0 | 0 | 10 | 100 | 40 | 20 | 20 | 20 |

0 = no injury
100 = entire killing
pre = pre-emergence
post = post-emergence

TABLE III

| Active ingredient | Dose g./ha. | green g. | relative % |
|---|---|---|---|
| Control (untreated) | — | 553 | 100 |
| Wuxal (known) | 5000 | 562 | 101 |
| Example 3 | 5000 | 393 | 71 |
| Example 3 | 1000 | 563 | 102 |
| Example 3 | 100 | 604 | 109 |

The results show that the new herbicides containing the complexes according to the invention show in case of green house tests in case of pre-emergence treatment at least the same activity as the known comparative agent and in case of post-emergence treatment they are more effective, they kill well the dicotyledonous weeds and in free land tests they are effective at smaller rates than the known agent and in monocotyledonous plants they kill well the monocotyledonous weeds. The selectivity of the known compositions is substantially the same as the selectively of the known compositions.

EXAMPLE VII

The plant growth regulating activity of the new herbicides is first of all important at small applied rates. In case of application as plant growth regulating agent the amount of the active ingredient amounts to under 100 g. pro ha.

EXAMPLE VIII

The applied amount of the new herbicides depends on the aim of the use of the character of weeds and the plants as well as on the wheather conditions. In case of pre-emergence treatment the amount of active ingredient is generally 70-300 g., preferably 100-200 g./ha. In case of post-emergence treatment the amount of active ingredient is generally 50-200 g., preferably 70-100 g./ha. The herbicides according to the invention can be used with other known plant protecting agents, preferably herbicides.

EXAMPLE IX

In case of free land small parcel tests we have found that in case of identical rates of active ingredients the complex according to Example 1 caused phytotoxid activity in the sixth month. Under free land conditions only in 5% whereas chlorosulfuron killed white mustard (*Sinapis alba*) in 65%.

It is known that chlorosulfuron (N-[6(6-methyl-4-methoxy-1,3,5-triazin-2-yl)-amino-carbonyl]-2-chlorobenzene-sulphonamide) is persistent at a dose of 20 g./ha. and therefore in the agricultural practice after winter wheat winter wheat has to be sawn. The complex according to the invention looses its activity by the vegetation of winter wheat as a consequence of the quicker decomposition and/or increased hydrophility due to the rapider dissolution from the surface-soil and afterwards in autumn any mono- or dicotyledonous plant can be sawn. The obtained results are summarized in Table IV.

TABLE IV

| Herbicide treatment | Dose g./ha. | % of killing *Sinapis alba* after treatment | | |
|---|---|---|---|---|
| | | 3 months | 6 months | 9 months |
| Control | — | 0 | 0 | 0 |
| Chlorosulfuron | 20 | 100 | 65 | 30 |
| Cyclodextrin-chlorosulfuron complex | 20 | 100 | 5 | 0 |

We claim:

1. A complex of benzenesulphonyl urea derivative of the general formula (II)

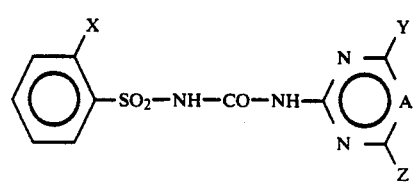

with β-cyclodextrin of the formula (I)

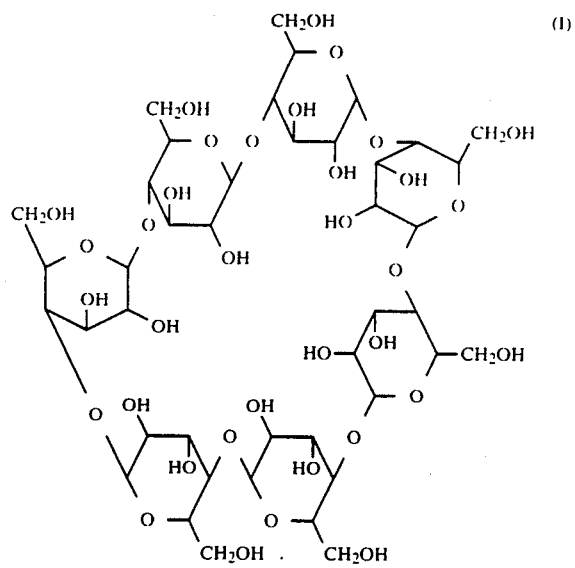

wherein the molar ratio of the components (II) and (I) is 1:2

X stands for halogen or —COOR, wherein R is an aliphatic group,

Y and Z stand for hydrogen, $C_{1-4}$ alkyl or $C_{1-4}$ alkoxy and

A stands for —$CH_2$— or nitrogen.

2. N[(4-methoxy-6-methyl-1,3,5-triazin-2-yl)aminocarbonyl]-(2-chlorobenzene)-sulphonamide β-cyclodextrin complex.

3. N-[(4-methoxy-6-methyl-1,3,5-triazin-2-yl)aminocarbonyl]-2-(methoxycarbonyl)-benzenesulphonamide β-cyclodextrin complex.

4. Herbicidal and plant growth regulating composition comprising as an active ingredient a complex of benzenesulphonyl urea of the general formula (II)

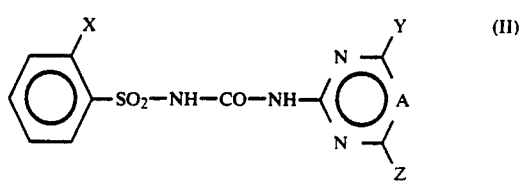

and β-cyclodextrin of the formula (I)

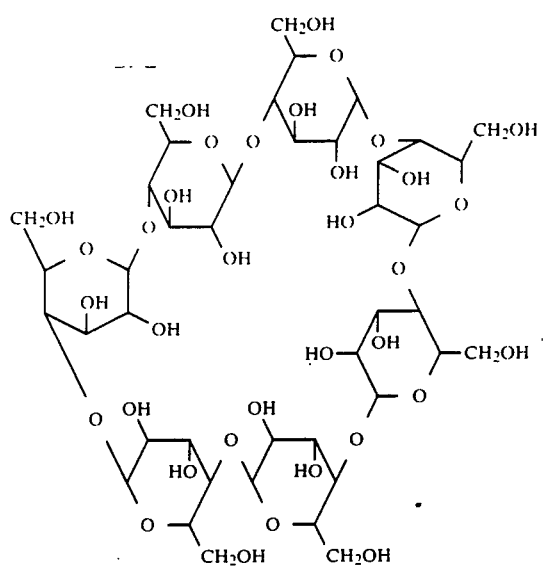

wherein

X stands for halogen or —COOR, wherein R is an aliphatic group,

Y and Z stand for hydrogen, $C_{1-14}$ alkyl or $C_{1-4}$ alkoxy and

A stands for —$CH_2$— or nitrogen.

5. A composition according to claim 4 comprising 0.1–95% by weight of active ingredient.

6. A herbicidal composition according to claim 5 comprising as active ingredient N-[(4-methoxy-6-methyl-1,3,5-triazin-2-yl)-aminocarbonyl](2-chlorobenzene)-sulphonamide β-cyclodextrin complex.

7. A plant growth regulating composition according to claim 4 comprising as active ingredient N-[(4-methoxy-6-methyl-1,3,5-triazin-2-yl)aminocarbonyl]-2-(methoxycarbonly)-benzenesulphonamide β-cyclodextrin complex.

8. Process for the preparation of the complex as claimed in claim 1 comprising reacting one mole of a benzenesulphonyl urea derivative of the general formula (II) —wherein X, Y, Z and A are as given in claim 1— with two moles of β-cyclodextrin.

9. A method of killing undesired plants which comprises treating the weeds or the soil with an effective amount of the composition containing the complex according to claim 1.

10. A process for stimulating plant growth which comprises treating the plants with an effective amount of the composition containing the complex according to claim 1.

* * * * *